United States Patent
Dantus et al.

(10) Patent No.: US 10,656,062 B2
(45) Date of Patent: May 19, 2020

(54) MATERIALS WITH DETECTABLE COMPRESSION MEMORY

(71) Applicant: BOARD OF TRUSTEES OF MICHIGAN STATE UNIVERSITY, East Lansing, MI (US)

(72) Inventors: Marcos Dantus, Okemos, MI (US); Gary J. Blanchard, Okemos, MI (US); Sheryl Blanchard, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 272 days.

(21) Appl. No.: 15/407,478

(22) Filed: Jan. 17, 2017

(65) Prior Publication Data
US 2017/0122855 A1    May 4, 2017

Related U.S. Application Data

(63) Continuation-in-part of application No. PCT/US2015/040883, filed on Jul. 17, 2015.
(Continued)

(51) Int. Cl.
*G01N 3/06* (2006.01)
*G01L 5/00* (2006.01)
(Continued)

(52) U.S. Cl.
CPC .......... *G01N 3/062* (2013.01); *A63B 69/3617* (2013.01); *A63B 71/06* (2013.01);
(Continued)

(58) Field of Classification Search
CPC ....... A42B 3/067; A61B 5/11; A63B 69/3617; A63B 71/06; A63B 71/08; A63B 71/10;
(Continued)

(56) References Cited

U.S. PATENT DOCUMENTS

| | | | | |
|---|---|---|---|---|
| 4,903,991 A | * | 2/1990 | Wright | B42D 25/29 283/70 |
| 5,040,313 A | * | 8/1991 | Sinnjian et al. | A43B 3/00 36/114 |

(Continued)

FOREIGN PATENT DOCUMENTS

WO    WO 2014/008031 A1 *  9/2014  ............... B32B 5/16

OTHER PUBLICATIONS

PCT/US2015/040883, Written Opinion of the International Search Authority, dated Oct. 9, 2015, 7 pages (Year: 2015).*

(Continued)

*Primary Examiner* — Jonathan M Dunlap
(74) *Attorney, Agent, or Firm* — Marshall, Gerstein & Borun LLP

(57) ABSTRACT

The disclosure relates to an irreversible dosimetric shock-detection substrate as well as related articles and methods. The shock-detection substrate incorporates a plurality of microcapsules serving as an irreversible means for detecting impact on the substrate. A shock above a characteristic threshold level experienced by the substrate induces an irreversible detectable change associated with the microcapsules upon shock-induced rupture. The irreversible detectable change provides a tamper-proof and non-electronic means for detecting a shock or impact. The shock-detection substrates can be incorporated into a variety of articles and used in a variety of settings, for example to monitor personal safety, to monitor article integrity, to monitor the end of the useful life of the shock-detection substrate itself, or in any other setting where it is desirable to irreversibly detect and/or localize a shock event.

31 Claims, 4 Drawing Sheets

Related U.S. Application Data

(60) Provisional application No. 62/026,765, filed on Jul. 21, 2014.

(51) Int. Cl.
```
A63B 71/10      (2006.01)
A42B 3/06       (2006.01)
A63B 71/08      (2006.01)
A63B 69/36      (2006.01)
A63B 71/06      (2006.01)
A61B 5/11       (2006.01)
A63B 102/24     (2015.01)
A63B 102/18     (2015.01)
A63B 102/32     (2015.01)
```

(52) U.S. Cl.
CPC ............ *A63B 71/08* (2013.01); *G01L 5/0052* (2013.01); *A42B 3/067* (2013.01); *A61B 5/11* (2013.01); *A63B 71/10* (2013.01); *A63B 2071/0694* (2013.01); *A63B 2102/18* (2015.10); *A63B 2102/24* (2015.10); *A63B 2102/32* (2015.10); *A63B 2209/00* (2013.01)

(58) Field of Classification Search
CPC ........ A63B 2071/0694; A63B 2102/18; A63B 2102/24; A63B 2102/32; A63B 2209/00; G01L 5/0052; G01N 3/062
USPC ........................................................ 116/203
See application file for complete search history.

(56) References Cited

U.S. PATENT DOCUMENTS

| | | | | |
|---|---|---|---|---|
| 5,343,569 | A * | 9/1994 | Asare | A42B 3/0433 2/411 |
| 9,572,389 | B2 * | 2/2017 | Twardowski et al. | A42B 3/063 |
| 2006/0063125 | A1 * | 3/2006 | Hamilton | A61C 9/00 433/70 |
| 2008/0009556 | A1 * | 1/2008 | Schneider et al. | C08G 18/10 521/128 |
| 2012/0009391 | A1 * | 1/2012 | Dry | B29C 73/22 428/188 |
| 2012/0226197 | A1 * | 9/2012 | Sanders et al. | A61F 2/7812 600/587 |
| 2014/0045962 | A1 * | 2/2014 | Schofalvi | C08J 9/0066 521/159 |
| 2014/0099472 | A1 * | 4/2014 | Greenhill | F42D 5/045 428/147 |
| 2015/0223544 | A1 * | 8/2015 | Rosenthal et al. | A42B 3/067 2/411 |
| 2017/0029625 | A1 * | 2/2017 | Stolarz, Jr. et al. | C09D 5/00 |

OTHER PUBLICATIONS

Kamata et al., "Synthesis and Characterization of Monodispersed Core—Shell Spherical Colloids with Movable Cores," *J. Am. Chem. Soc.*, 125:2384-85 (2003).

Kijewska et al., "Photopolymerized Polypyrrole Microvessels," *Chem. Eur. J.*, 18:310-20 (2012).

Tiarks et al., "Preparation of Polymeric Nanocapsules by Miniemulsion Polymerization," *Langmuir*, 17:908-18 (2001).

Wang et al., "Template Synthesis of Nanostructured Materials via Layer-by-Layer Assembly," *Chem. Mater.*, 20:848-58 (2008).

* cited by examiner

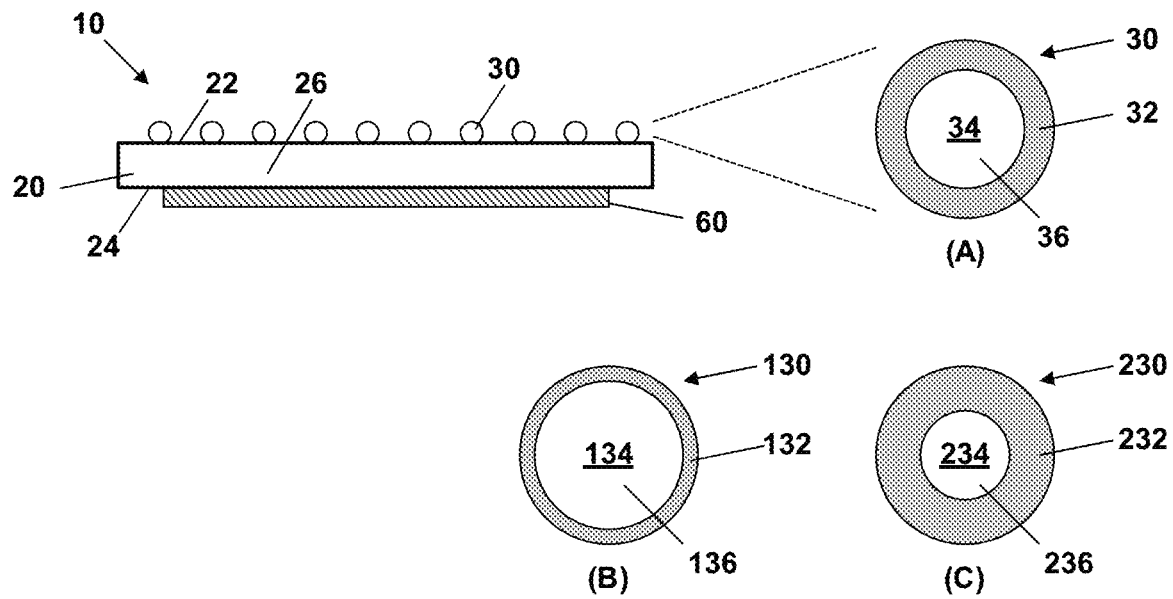
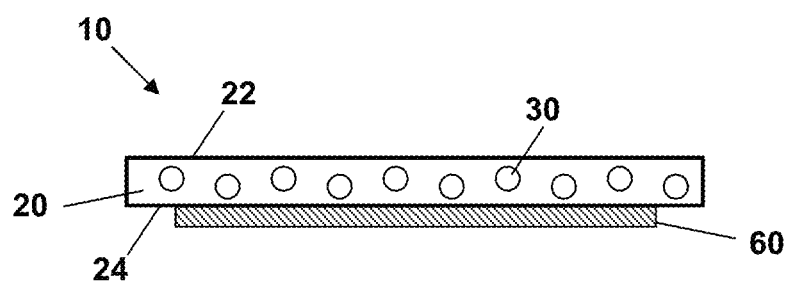
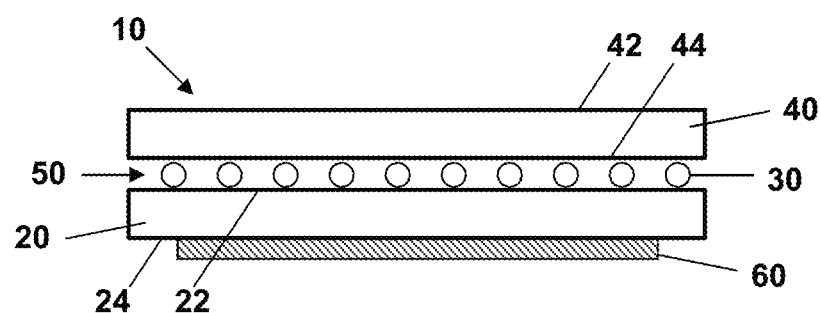
Figure 1
Figure 2
Figure 3

MATERIALS WITH DETECTABLE COMPRESSION MEMORY

CROSS REFERENCE TO RELATED APPLICATION

This application is a continuation-in-part of International Application No. PCT/US15/40883 filed Jul. 17, 2015, which in turn claims priority to U.S. Provisional Application No. 62/026,765 filed Jul. 21, 2014, both of which are incorporated herein by reference in their entireties.

STATEMENT OF GOVERNMENT INTEREST

None.

BACKGROUND OF THE DISCLOSURE

Field of the Disclosure

The disclosure relates to materials and articles that provide an irreversible history of compression forces experienced by the materials and articles. The disclosure relates more particularly to an irreversible dosimetric shock-detection substrate as well as related articles and methods. The shock-detection substrates can be incorporated into a variety of articles and used in a variety of settings, for example to monitor personal safety, to monitor article integrity, and/or to monitor the end of the useful life of the shock-detection substrate itself.

SUMMARY

In one aspect, the disclosure relates to an irreversible dosimetric shock-detection substrate comprising: (a) a first substrate having (i) a top surface, (ii) an opposing bottom surface, and (iii) an interior substrate volume between the top surface and the bottom surface; and (b) a plurality of microcapsules each comprising (i) an outer shell defining an interior volume and (ii) an indicator contained in the interior volume, wherein: the microcapsules are positioned at one or more of (i) the first substrate top surface, (ii) the interior substrate volume, and (iii) the first substrate bottom surface, and each microcapsule has a characteristic impact threshold prior to rupture of the microcapsule and release of the indicator from the interior volume to generate an irreversible change in a detectable property associated with the indicator. In a refinement, the microcapsules are positioned at the first substrate top surface, and the shock-detection substrate further comprises (c) a second substrate positioned above the microcapsules positioned at the first substrate top surface, such that the microcapsules positioned at the first substrate top surface form an intermediate microcapsule layer between the first substrate and the second substrate. In another refinement, the shock-detection substrate further comprises a means for attachment on one or both of an outer surface of the first substrate and an outer surface of the second substrate.

Various refinements of the shock-detection substrate are possible. For example, the at least one of the first substrate and the second substrate can be optically translucent or transparent. In another refinement, the characteristic impact threshold of the microcapsule has been selected by controlling one or more of reaction solvent, polymerization initiator, monomer, ionic strength, reaction medium pH, reaction temperature, reaction time, and UV light exposure during a polymerization process forming the microcapsule. In another refinement, the detectable property is selected from the group consisting of an optical property, an olfactory property, a chemical property, an electrical property, an electromagnetic property, and combinations thereof. In another refinement, the shock-detection substrate further comprises a means for attachment on one or both of the first substrate top surface and the first substrate bottom surface. In another refinement, the plurality of microcapsules is spatially positioned on the substrate to define one or more padding protection areas containing the plurality of microcapsules, the one or more padding protection areas having a shape corresponding to protective padding for a protective garment.

In a particular refinement, the plurality of microcapsules comprises: (A) a plurality of first microcapsules containing a first indicator therein and having a first characteristic impact threshold; and (B) a plurality of second microcapsules containing a second indicator therein and having a second characteristic impact threshold; wherein: the detectable property of the first indicator is different from the detectable property of the second indicator, and the first characteristic impact threshold is different from the second characteristic impact threshold. In an embodiment, the plurality of the first microcapsules and the plurality of the second microcapsules are homogeneously distributed throughout a region of the first substrate. In another embodiment, the plurality of the first microcapsules and the plurality of the second microcapsules are spatially segregated in separate regions of the first substrate.

In another aspect, the disclosure relates to a protective garment (e.g., a helmet or a wearable guard for other than a head body part) comprising the shock-detection substrate according to any of the various embodiments spatially positioned in or on the protective garment to detect shock experienced by a wearer of the protective garment. In a particular embodiment, the protective garment comprises: (a) a protective shell having (i) an outer surface and (ii) an opposing inner surface; (b) protective padding having (i) an outer surface, (ii) an opposing inner surface, and (iii) an interior padding volume between the outer surface and the inner surface, wherein the protective padding is mounted at the outer surface thereof to the protective shell at the inner surface thereof; and (c) the shock-detection substrate according to any of the various embodiments positioned at one or more of: (i) an interface between the protective shell inner surface and the protective padding outer surface, (ii) the interior padding volume, (iii) the protective padding inner surface, and (iv) the protective shell outer surface. In a refinement, the protective shell comprises a viewport configured to provide optical access from the protective shell outer surface to the interface between the protective shell inner surface and the protective padding outer surface. In another refinement, the shock-detection substrate is positioned at the interface between the protective shell inner surface and the protective padding outer surface. In another refinement, the shock-detection substrate is positioned at the protective padding inner surface.

In another aspect, the disclosure relates to a method for equipping a protective garment with a means for detecting impact, the method comprising: (a) providing a protective garment according to any of the various embodiments; (b) attaching the shock-detection substrate according to any of the various embodiments to one or more of: (i) the protective padding outer surface, and (ii) the protective padding inner surface; and (c) mounting the protective padding at the outer surface thereof to the protective shell at the inner surface thereof (e.g., mounting the padding to the protective shell after the shock-detection substrate is attached; mounting the padding to the protective shell and then attaching the shock-detection substrate to the inner padding surface).

In another aspect, the disclosure relates to a kit comprising: (a) a shock-detection substrate according to any of the various embodiments; and (b) protective padding sized and shaped for insertion into a protective shell of a protective garment, the protective padding having (i) an outer surface, (ii) an opposing inner surface, and (iii) an interior padding volume between the outer surface and the inner surface. In a refinement, the shock-detection substrate includes a plurality of substrates, which can be correspondingly shaped for the protective padding in the kit (e.g., substrate as a whole or padding protection areas on the substrate). In another refinement, the shock-detection substrate can be a unitary substrate sheet intended to be cut as desired for application to padding. In another refinement, the protective padding includes a plurality of padding units.

In another aspect, the disclosure relates to a method for detecting impact on a protective garment worn by a user, the method comprising: (a) wearing the protective garment according to any of the various embodiments (e.g., a user wearing the protective garment during participation in sport or other contact activity); (b) impacting the protective garment (e.g., resulting from contacting or colliding with another sport participant or the environment); (c) interrogating the means for detecting impact of the protective garment after (b) to determine whether the protective garment has sustained an impact force exceeding a characteristic impact threshold of the microcapsules (e.g., evaluation, observation, measurement, etc. of one or more of the particular detectable property(ies) of the shock-detection substrate, such as by human observation (e.g., visual), machine-assisted detection; step of interrogating can be during or after game). In a refinement, the method further comprises (d) if the protective garment has sustained an impact force exceeding the characteristic impact threshold, performing one or more of (i) removing the user from an ongoing impact environment (e.g., an ongoing sporting contest where the user is removed from further game participation), (ii) investigating the user for an impact-related injury, and (iii) treating the user for an impact-related injury (e.g., a concussion for helmet protective garments; a bone fracture, internal bleeding or other physical damage for the corresponding protective garment body parts more generally).

In another aspect, the disclosure relates to a shipping or storage container comprising the shock-detection substrate according to any of the various embodiments spatially positioned in or on the container to detect shock experienced by the container during shipment or storage.

In another aspect, the disclosure relates to an electronic apparatus comprising the shock-detection substrate according to any of the various embodiments spatially positioned in or on the apparatus to detect shock experienced by the apparatus during shipment, storage, or use.

In another aspect, the disclosure relates to a method for forming a dental bite pattern, the method comprising: (a) providing the shock-detection substrate according to any of the various embodiments; and (b) applying biting pressure from teeth to the shock-detection substrate, thereby rupturing at least some of the microcapsules and generating the associated detectable property in a spatial pattern corresponding to the dental bite pattern of the teeth.

In another aspect, the disclosure relates to a piece of sports striking equipment comprising the shock-detection substrate according to any of the various embodiments spatially positioned in or on the equipment to detect shock experienced by the equipment during use.

In another aspect, the disclosure relates to a method for validating a handwritten signature, the method comprising: (a) providing a physical written document comprising the shock-detection substrate according to any of the various embodiments; (b) receiving a handwritten signature on the shock-detection substrate to form tamper-proof recording of the handwritten signature; and (c) comparing the tamper-proof recording of the handwritten signature with a known reference of the handwritten signature.

While the disclosed articles, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein:

FIG. 1 is a side cross sectional view of a shock detection substrate according to the disclosure and incorporating microcapsules on an exterior surface of the substrate, where insets A, B, and C illustrate different microcapsule structures.

FIG. 2 is a side cross sectional view of a shock detection substrate according to an additional aspect of the disclosure and incorporating microcapsules within the interior substrate volume.

FIG. 3 is a side cross sectional view of a shock detection substrate according to an additional aspect of the disclosure and incorporating multiple substrates.

DETAILED DESCRIPTION

Figure 4:
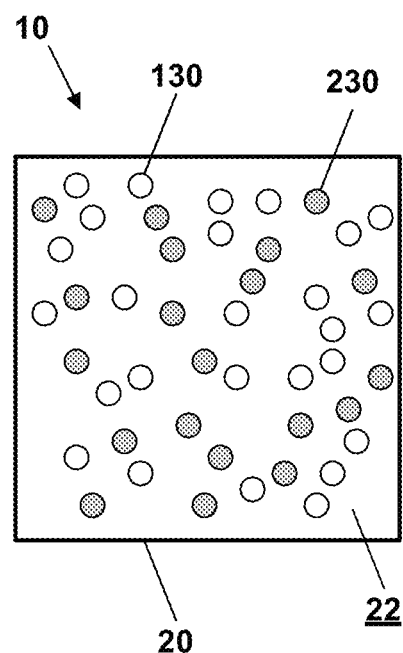
FIG. 4 is a top view of a shock detection substrate according to an additional aspect of the disclosure and incorporating a plurality of different microcapsule types homogeneously distributed throughout a substrate surface.

The disclosure relates to an irreversible dosimetric shock-detection substrate as well as related articles and methods incorporating the same. The shock-detection substrate incorporates a plurality of microcapsules serving as an irreversible means for detecting impact on the substrate. Shock detection is irreversible in the sense that a shock (e.g., shearing or impact force) experienced by the substrate above a characteristic threshold level induces an irreversible detectable change associated with the microcapsules upon shock-induced rupture (e.g., release of a detectable color indicator, among other options, as described below). The microcapsules impart compression memory to the shock-detection substrate, because the shock-induced rupture of the microcapsule provides a permanent, detectable indication of the shock event (e.g., the occurrence of the event and/or the location of the event), even after the shock event is completed. The irreversible detectable change further provides a tamper-proof and non-electronic means for detecting a shock or impact. The shock-detection substrates can be incorporated into a variety of articles and used in a variety of settings, for example to monitor personal safety, to monitor article integrity, or in any other setting where it is desirable to irreversibly detect a shock event (e.g., further detecting the location of the same).

In an embodiment, the shock-detection substrate incorporates the microcapsules into a foamed substrate which itself can be used as padding or cushioning in a garment or article. The shock-detection substrate itself in this case provides the ability to detect compression-based end-of-life for its use as padding or cushioning. The incorporated microcapsules burst when exposed to excessive force and can release an indicator therein to provide a detectable indication that the force threshold has been exceeded. When initially formed, foam materials have a mechanical resiliency or resistance to deformation that degrades over time as the foam material ages and/or is used in compression cycles under normal loads. The foam material and the microcapsules are selected such that the initial resiliency of the foam is high enough such that under normal loads and deformation/compression, the foam is strong enough to prevent rupture of the microcapsules within the foam interior. As the foam ages and its resiliency is diminished (e.g., through normal aging and/or cyclic stress-induced degradation), the microcapsules are exposed to comparatively and increasingly higher deformation/compression under the same normal usage loads, and the microcapsules eventually rupture to release their indicator. Release of the indicator can thus be viewed as indication that the shock-detection substrate has reached the end of its useful life as a padding or cushioning component (i.e., it need not necessarily indicate risk to personal safety), and either the substrate or its corresponding article can be replaced with a new component. This embodiment provides a non-destructive manner to determine (e.g., by visual inspection or otherwise) whether a shock-detection substrate has reached the end of its useful life as a padding or cushioning component. The shock-detection substrate in this embodiment can be incorporated as a padding or cushioning component into an article such as footwear (e.g., as an insole padding component), a wearable prosthetic limb (e.g., as padding or cushion component for the wearer's comfort), a multiple-use packing material, and a protective garment (e.g., where microcapsule rupture can indicate end-of-life failure and not a high-intensity impact as a personal safety risk).

FIGS. 1-6 illustrate several embodiments of a shock-detection substrate 10 according to the disclosure.

With specific reference to FIGS. 1-3, the shock-detection substrate 10 includes a first substrate 20 having a top surface 22, an opposing bottom surface 24, and an interior substrate volume 26 between the top surface 22 and the bottom surface 24. A plurality of microcapsules 30 are positioned at one or more of the first substrate top surface 22, the interior substrate volume 26, and the first substrate bottom surface 24. Each microcapsule 30 has a characteristic impact threshold (e.g., based in its physical, mechanical, and chemical properties, as described below) which corresponds to a threshold shock event above which the irreversible, detectable change associated with the microcapsule 30 and shock-detection substrate 10 takes place. As illustrated in FIG. 1, the microcapsules 30 are positioned at the first substrate 20 top surface 22 (e.g., immobilized on the top surface 22 with an adhesive or otherwise). FIG. 2 illustrates an embodiment in which the microcapsules 30 are positioned within the interior substrate volume 26 of first substrate 20 (e.g., distributed throughout the first substrate 20 as a composite material). FIG. 3 illustrates an embodiment in which the shock-detection substrate 10 includes a second substrate 40 having a top surface 42, an opposing bottom surface 44, and an interior substrate volume 46 between the top surface 42 and the bottom surface 46. The second substrate 40 is positioned above the microcapsules 30 (e.g., immobilized on the bottom surface 44 with an adhesive or otherwise) positioned at the first substrate 20 top surface 22. The microcapsules 30 form an intermediate microcapsule layer 50 between the first substrate 20 and the second substrate 40.

The first substrate 20 and the second substrate 40 are not particularly limited and may be formed from the same or different materials. The substrates can be thin, rigid or flexible materials such as polymer materials (e.g., sheet or film) or cellulosic materials (e.g., paper or cardstock). The substrates can be opaque, optically translucent, or transparent. In some embodiments, at least one of the first substrate 20 and the second substrate 40 is optically translucent or transparent. For example, in the embodiment illustrated in FIG. 2, the first substrate 20 can be optically translucent or transparent, in particular when the microcapsules 30 include an optical indicator 34 that becomes optically or visibly detectable through the substrate 20 matrix upon rupture of the microcapsules 30. Similarly, in the embodiment illustrated in FIG. 3, the second substrate 40 can be optically translucent or transparent, such as when the microcapsules 30 include an optical indicator 34 that becomes optically or visibly detectable through the substrate 40 upon rupture of the microcapsules 30 (e.g., where the second substrate 40 represents an optical interrogation surface/direction and the first substrate 20 is simply a support substrate, which can be opaque or otherwise).

In a particular refinement of the embodiment illustrated in FIG. 2, the first substrate 20 can be formed from or otherwise include a foam material throughout which the microcapsules 30 are positioned within the interior substrate volume 26 thereof. The foam material is not particularly limited, and it can generally be any flexible foam used for padding or cushioning, for example whether for protection or comfort of a user wearing a garment or article incorporating the foam material. In various refinements, the foam material can be formed from a thermoplastic polymeric material or a (crosslinked) thermoset polymeric material. Further, the foam material can have an open cell structure (e.g., an open cell foam network of interconnected pores), a closed cell structure (e.g., discrete, generally non-connected pores), or a combination of both (e.g., some interconnected pore networks and some discrete, isolated pores). For thin foam films, the fluid indicator 36 should be visible upon microcapsule 30 rupture, regardless of whether the foam material has an open cell structure or a closed cell structure. In certain embodiments, for example when the microcapsules 30 contain a fluid indicator 36, an open cell structure for the foam can provide a means for capillary transport of fluid indicator upon microcapsule 30 rupture so that the indicator 36 can be transported throughout the interior substrate volume 26 of the foam to an exterior surface 22, 24 thereof where it can be more easily detected (e.g., whether by visible or optical detection means or otherwise).

The specific polymeric materials used for the foam substrate 20 are not particularly limited and can include any conventional polymeric foams. Examples of suitable polymeric materials that can be used for the foam substrate 20 include polyurethanes, poly(vinyl nitriles), polyethylenes (e.g., HDPE, LDPE), polypropylenes, other polyolefins, polystyrenes, poly(ethylene-vinyl acetates), poly(vinyl chlorides), poly(acrylonitrile-butadiene-styrenes), polyimides, polyetherimides, polyphenyleneoxides, polychloroprenes, polysiloxanes, polyepoxides, polyesters (e.g., aliphatic, aromatic, or aliphatic-aromatic), phenolic resins, urea-formaldehyde resins, cellulose acetates, and combinations thereof (e.g., as blends thereof; as block- or random-copolymers of monomers thereof). Examples of particularly suitable polymeric foam materials include (thermoplastic) polyurethane foams, poly(vinyl nitrile) foams, and poly(ethylene-vinyl acetate) foams.

The shock-detection substrate 10 in the form of a foam material including the foam substrate 20 with the microcapsules 30 therein can be formed according to any suitable conventional foam processing methods, such as blowing, extrusion, molding, etc. For example, the polymeric material used for the foam substrate 20 can be combined or mixed with (already formed) microcapsules 30 along with a suitable blowing agent (e.g., chemical, physical, or other conventional gas blowing agent) and then blown, extruded, molded, etc., into a foam substrate 20 containing the microcapsules 30 distributed throughout the interior substrate volume 26. At the point when combined with microcapsules 30 and blowing agent, the polymeric material used for the foam substrate 20 can be in the form of a thermoplastic polymer melt, a liquid blend of monomers, comonomers, and/or prepolymers (e.g., which then will polymerize during the foaming process, such as to form a thermoplastic or thermoset polymeric foam), etc.

The shock-detection substrate 10 further can include an attachment means 60 disposed on any or several of its outer exposed surfaces, for example on the bottom surface 24 of the first substrate 20 as illustrated in FIGS. 1-3. The attachment means 60 is not particularly limited and can include any conventional means for fixedly or removably mounting/attaching two surfaces, such as an adhesive coating (e.g., pressure-sensitive adhesive, cured/dried glue composition) or a mechanical fastener (e.g., snaps, buttons, hook-and-loop fasteners, rivets, screws, etc.). The shock-detection substrate 10 can include different types of attachment means 60, for example when more than one outer exposed surface includes the means 60.

As illustrated in inset A of FIG. 1, a microcapsule 30 includes an outer shell 32 which defines (or encloses) an interior volume 34 of the microcapsule 30. An indicator 36 associated with the irreversible detectable change of the microcapsule 30 and shock-detection substrate 10 is contained in the interior volume 34. The microcapsule 30 can be generally spherical in shape or otherwise, such as a cylindrical rod or disk, a prolate or oblate spheroid, etc. Suitable microcapsule 30 sizes are on the nanometer- or micrometer-scale, for example having a number-, volume-, or weight-based average, mean, median, or other characteristic size (e.g., diameter) in a range of about 10 nm to about 10 μm (e.g., at least 10 nm, 20 nm, 50 nm, 100 nm, or 200 nm and/or up to 100 nm, 200 nm, 500 nm, 1 μm, 2 μm, 5 μm, or 10 μm). The interior volume 34 is suitably sealed/closed relative to the external environment by the microcapsule 30 outer shell 32. The outer shell 32 is suitably a polymeric shell material (e.g., an electrically conductive polymer or an electrically non-conductive polymer), such as polypyrrole, poly(methyl methacrylate), poly(benzyl methacrylate), poly(lactic acid), poly(acrylic acid), polyaniline, polysiloxane (e.g., networked or crosslinked silicone resin), or otherwise. The indicator 36 is suitably contained within a fluid medium (e.g., water medium, water-containing medium, organic solvent medium such as a hydrophobic solvent/liquid or hydrophilic solvent/liquid, and mixtures thereof) inside the interior volume 34. The indicator 36 is suitably a colorant such as a non-toxic colorant. The indicator 36 can be dissolved, dispersed, emulsified, or otherwise mixed in the fluid medium. The fluid medium is suitably a non-toxic and/or a non-volatile carrier which can liquid and/or gel components.

The microcapsule 30 can be formed by any suitable method known in the art, for example including emulsion polymerization from an emulsion containing a fluid medium with the indicator 36 therein and at least one monomer corresponding to an outer shell 32 polymer. As the monomer is polymerized, it forms the shell 32 containing the indicator 36 therein. Kijewska et al. (2012), incorporated herein by reference, describes a suitable method of microcapsule 30 formation, which includes the photo-initiated emulsion polymerization of pyrrole monomer to form polypyrrole microcapsules 30 of relatively uniform size and containing any of a variety of materials (e.g., dyes, magnetic nanoparticles, ionic species) from the polymerization medium. Other suitable methods of microcapsule formation are described in Tiarks et al. (2001), Kamata et al. (2003), and Wang et al. (2008), all of which are incorporated herein by reference.

In an illustrative embodiment, the indicator 36 can include a hydrophobic colorant such as an oil-based paint, dye, or pigment in a hydrophobic liquid medium. Examples of suitable hydrophobic liquid media include oils such as vegetable oils (e.g., canola oil). The indicator 36 is a water-immiscible mixture which is then added to an aqueous reaction medium, which can include one or more water-miscible organic solvents (e.g., an alcohol-water mixture such as ethanol-water). The indicator 36 is then mixed or otherwise agitated with the aqueous reaction medium to form an emulsion of indicator 36 droplets in the reaction medium. The specific size (or size distribution) of indicator 36 droplets in the reaction medium can be selected or controlled, for example, by varying one or more of the degree of agitation or mixing, the selection and relative weight ratio of alcohol (or other water-miscible organic solvent) and water in the reaction medium, the weight ratio of reaction medium to the total indicator 36 added thereto, the selection of the hydrophobic liquid medium for the indicator 36, etc. Monomers for formation of a polymeric shell 32 are then added to the indicator 36 emulsion reaction medium along with any co-reactants, catalysts, and/or initiators desired for the polymerization. For example, pyrrole monomer and an aqueous iron (III) chloride oxidant solution can be added to the reaction medium. When polymerization is initiated the polymer (e.g., polypyrrole) forms as a shell 32 around the indicator emulsion 36 droplets, thereby forming a suspension of the microcapsules 30 in the reaction medium. The microcapsule 30 size and characteristic impact threshold can be controlled or selected, for example by varying one or more of the reaction/polymerization time, relative amount of monomer added to the reaction medium, and the emulsion droplet size. Once the polymerization reaction is complete, the microcapsules 30 can be collected/ separated from the reaction medium by any suitable means (e.g., filtration) and incorporated into the shock detection substrate 10 as generally described herein.

In an embodiment, the microcapsule 30 can have a (polymeric) silica outer shell 32. Specifically, the silica outer shell 32 can be formed from a networked or crosslinked silicone resin, for example resulting from the emulsion polymerization of silicone resin monomers in the presence of indicator 36 droplets in the reaction medium as described above. Suitable silicone resin monomers include silicates that can hydrolyze and then condense in an aqueous emulsion reaction medium to form the networked silicone resin (e.g., characterized by networked —SiO— repeating units) as the silica outer shell 32 encasing the indicator emulsion 36 droplets. Examples of specific silicates useful as such monomers include alkyl silicates with at least two, preferably at least three or four (e.g., three or four) hydrolyzable alkoxy groups. A general alkyl silicate is represented by the formula $Si(OR^1)_m(R^2)_{4-m}$, where m is 2, 3, or 4. In various reaction systems, one, two, three, or more different alkyl silicate species can be in used admixture as comonomers (e.g., alkyl silicates of the foregoing formula where at least one of $R^1$, $R^2$, and m are different between different alkyl silicate species). The $OR^1$ groups represent the hydrolyzable alkoxy groups, where two $OR^1$ groups (i.e., m=2) in a given silicate monomer promote polymeric chain growth or extension, while three or four $OR^1$ groups (i.e., m=3 or 4) in a given silicate monomer promote the growth of crosslinked or networked polymeric side chains. $R^1$ can be the same or different in each of the several $OR^1$ groups (e.g., when m=4, $R^1$ in each of the four $OR^1$ groups can be the same or different as $R^1$ in the other $OR^1$ groups). $R^1$ is generally an alkyl group, for example a linear or branched alkyl group with at least 1, 2, or 3 carbon atoms and/or up to 3, 4, 6, 9, or 12 carbon atoms (e.g., methyl, ethyl, propyl, isopropyl, butyl, isobutyl, tert-butyl, etc.). The $R^2$ groups, when present, can be the same or different and are generally non-hydrolyzable, substituted or unsubstituted, alkyl or alkenyl groups, for example a linear or branched, substituted or unsubstituted, alkyl or alkenyl group with at least 1, 2, or 3 carbon atoms and/or up to 3, 4, 6, 9, or 12 carbon atoms. The $R^2$ groups can be substituted with one or more ether groups, carbonyl groups, ester groups, hydroxy groups, an amino groups, such as at an interior location of the $R^2$ group chain and/or at a terminal location of the $R^2$ group chain (e.g., on the opposite chain end relative to the silicon atom). Inclusion of the non-hydrolyzable silicate $R^2$ group and selection of its chemical structure can provide control over resulting properties of the microcapsule 30, for example including one or more properties such as polarity, propensity to aggregate, etc. Additionally, for multi-step growth processes, the presence of non-hydrolyzable groups provides sites for attachment of functional groups and/or subsequent layers of material, if desired. For example, an $R^2$ group including an amino functional group (e.g., an aminoalkyl group such as in aminopropyltriethoxysilane or aminopropyltrimethoxysilane) can provide polar character to the resulting microcapsule 30. Similarly, an alkenyl $R^2$ group can provide a means for further vinyl polymerization of an outer polymer shell over the inner silica shell, such as with a (meth)acrylic or (meth)acrylate monomer, ethylene, propylene, or other olefin monomer, etc.

The specific alkyl silicates used are not particularly limited and can generally include those known for use in hydrolysis and condensation reactions to form silicones, silica, etc. Example alkyl silicates include tetraethylorthosilicate (TEOS; $R^1$ is $C_2H_5$ and m is 4), tetramethylorthosilicate (TMOS; $R^1$ is $CH_3$ and m is 4), aminopropyltriethoxysilane (APTES; $R^1$ is $C_2H_5$, m is 3, and $R^2$ is $C_3H_6NH_3$), aminopropyltrimethoxysilane (APTMS; $R^1$ is $CH_3$, m is 3, and $R^2$ is $C_3H_6NH_3$), octadecyl trimethoxysilane ($R^1$ $CH_3$, m is 3, and $R^2$ is n-$C_{18}H_{37}$), vinyl triethoxysilane ($R^1$ is $C_2H_5$, m is 3, and $R^2$ is $CH=CH_2$ (vinyl)), and methoxy terminated-poly(ethylene glycol) (MPEG)-triethoxysilane ($R^1$ is $C_2H_5$, m is 3, and $R^2$ is methoxy terminated-poly (ethylene glycol)).

An example process for forming silica microcapsules 30 is as follows. An oil-soluble dye is dissolved in an oil or other hydrophobic liquid of interest to form an indicator 36 as above. An aliquot of the dye-containing oil indicator 36 is then added to a mixture of neat tetraethylorthosilicate (TEOS) and neat aminopropyltriethoxysilane (APTES) silica monomers at a desired molar ratio. The selected molar ratio range can vary broadly, for example ranging from 1:100 APTES:TEOS to 1:1 APTES:TEOS. Similar ranges apply to other silane mixtures (e.g., where the APTES amount can be representative of another silane with a functional group other than alkoxy and/or alkyl, and the TEOS amount can be representative of another silane with only alkoxy and/or alkyl functional groups). The molar ratio can be selected to control rigidity, aggregation properties, and/or surface chemical reactivity of the microcapsules 30. The oil and silicate/silane reagents are immiscible and initially separated; subsequent mechanical agitation is used to produce an emulsion of the oil indicator 36 droplets in the liquid monomer medium. An aliquot of the TEOS/APTES/ dye-containing oil suspension is then introduced into an aqueous solution of a surfactant such as cetyltrimethylammonium bromide (CTAB) at a selected molar concentration. The concentration of the surfactant can be selected as desired (e.g., up to about 0.1 M, whether for CTAB or other surfactant) to control the formation and size of the suspended oil droplets that get coated with the siloxane (e.g., which generally corresponds to the resulting microcapsule 30 size). This mixture is vortexed or otherwise further agitated to mix the dye oil indicator 36 droplets into the formed emulsion of the TEOS/APTES and aqueous CTAB system. Upon exposure to water in the aqueous surfactant solution, the alkoxy groups of the TEOS/APTES reagents hydrolyze to their silanol analogs and then condense to form a polymerized silica network as the outer shell 32 on the surface of the suspended dye oil indicator 36 droplets. The CTAB functions as a surfactant to stabilize the oil indicator 36 droplets and keeps them separated during the active polymerization process. After vortexing, the solution is allowed to settle. The emulsion resolves during settling into a system which contains dye-containing oil indicator 36 droplets encapsulated in silica shell 32 microspheres 30 and an aqueous phase. The duration of the silane encapsulating reaction is related to the thickness of the resulting siloxane layer as the outer shell 32 covering the oil indicator 36 droplets, and the reaction time can be suitably selected to control shell 32 thickness to have a desired characteristic impact threshold.

Each microcapsule 30 has a characteristic impact threshold prior to rupture of the microcapsule 30 and release of the indicator 36 from the interior volume 34 to generate an irreversible change in the detectable property associated with the indicator 36. When the microcapsule 30 experiences an impact force below the threshold value, the shock is absorbed by the microcapsule 30 (e.g., possibly causing it deform (reversibly or irreversibly), but not rupture or otherwise break). When the microcapsule 30 experiences an impact force above the threshold value, the microcapsule 30 breaks, releasing the indicator 36 and causing the irreversible detectable impact event associated therewith. The characteristic impact threshold is generally a function of the mechanical properties of the microcapsule 30 and its contents. Factors affecting the impact threshold can include, for example, diameter (D) or other characteristic size of the microcapsule 30/outer shell 32, thickness (T) of the outer shell 32 wall, mechanical/strength properties of the shell 32 material, and the material contained within the interior volume 34. Depending on the particular method used for making the microcapsule 30, the microcapsule material and corresponding geometric parameters of the microcapsule can be suitably controlled or selected to obtain a desired impact threshold. For example, when using an emulsion polymerization process (e.g., UV photo-initiated emulsion polymerization), the characteristic impact threshold of the microcapsule 30 can be been selected by controlling or selecting one or more polymerization reaction conditions, such as reaction solvent, polymerization initiator, monomer, ionic strength of reaction medium, reaction medium pH, reaction temperature, reaction time, emulsion droplet size, and UV light exposure.

A plurality of microcapsules 30 similarly has a characteristic impact threshold distribution associated therewith, which can result from capsule-to-capsule variability for individual microcapsules 30. Suitably, the variability is small and the corresponding impact threshold distribution is relatively narrow, thus reducing the likelihood or impact of false negatives or false positives resulting from individual microcapsules 30 which are stronger or weaker than intended. For example, on a number-, volume-, or weight-basis, the plurality of microcapsules 30 suitably has a characteristic impact threshold distribution such that at least 75%, 90%, 95%, or 99% of the microcapsules 30 have an individual characteristic impact threshold that is within 1%, 5%, 10%, or 25% of an average (or mean or median) impact threshold of the distribution. The desirably narrow impact threshold distribution can be obtained by forming the microcapsules 30 with correspondingly narrow distributions related to diameter and wall thickness.

In some embodiments, the shock-detection substrate 10 can incorporate a single plurality of microcapsules 30, all of which microcapsules 30 in the plurality are characterized by a single impact threshold distribution (e.g., all microcapsules 30 may be represented by a single distribution as represented above). In other embodiments, the shock-detection substrate 10 can incorporate multiple different groups of microcapsules 30. For example, as illustrated in insets B and C of FIG. 1, a first microcapsule 130 includes an outer shell 132 which defines (or encloses) an interior volume 134 of the first microcapsule 130, and a second microcapsule 230 includes an outer shell 232 which defines (or encloses) an interior volume 234 of the second microcapsule 230. As qualitatively illustrated, the outer shell 132 is thinner than the outer shell 232, and the characteristic impact threshold of the first microcapsule 130 can be correspondingly smaller than that of the second microcapsule 230 (e.g., when the diameter and other properties of the two microcapsules 130, 230 are the same or substantially similar). Thus, in some embodiments, the shock-detection substrate 10 can include a plurality of the first microcapsules 130 having a first characteristic impact threshold and a plurality of the second microcapsules 230 having a second characteristic impact threshold (e.g., where the first characteristic impact threshold is different from the second characteristic impact threshold). Suitably, the detectable property of the first indicator 136 is different from the detectable property of the second indicator 236.

The first and second detectable properties can be different, for example, by using different indicators or by using the same indicators at different concentrations or in other ways to provide different responses. As noted above, different impact thresholds are controllable or selectable by varying wall thickness, microcapsule diameter, polymerization conditions, polymer selection, etc. In this way, microcapsules with different impact threshold levels and different detectable properties (e.g., different generated colors) allow for differentiation of low/high impacts. For example, the first characteristic impact threshold may be 100 units (e.g., arbitrary relative units corresponding to impact force), and the second characteristic impact threshold may be 200 units, where the threshold levels are selected to correspond to warning and damage levels, for instance. When the shock-detection substrate 10 is incorporated into an article, a detection corresponding to the low threshold may indicate the possibility of a damaging impact to the article sometime in the past (e.g., and the article should be inspected for damage), and a detection corresponding to the high threshold may positively indicate a damaging impact to the article sometime in the past (e.g., and the article should be rejected or discarded as damaged). Similarly, when the shock-detection substrate 10 is incorporated into a personal protective garment worn by a user, a detection corresponding to the low threshold may indicate the possibility of a damaging impact to the user (e.g., and the user may need medical attention), and a detection corresponding to the high threshold may positively indicate a damaging impact to the user (e.g., and the user should receive immediate medical attention). Although described in the context of two distinct types of microcapsules 130, 230, shock-detection substrates 10 according to the disclosure more generally can include any number of different microcapsule types (e.g., n different microcapsule types with n different detectable properties and/or n different impact thresholds, such as n being at least 2, 3, or 5 and/or up to 3, 5, 10, or 20).

Figure 5:
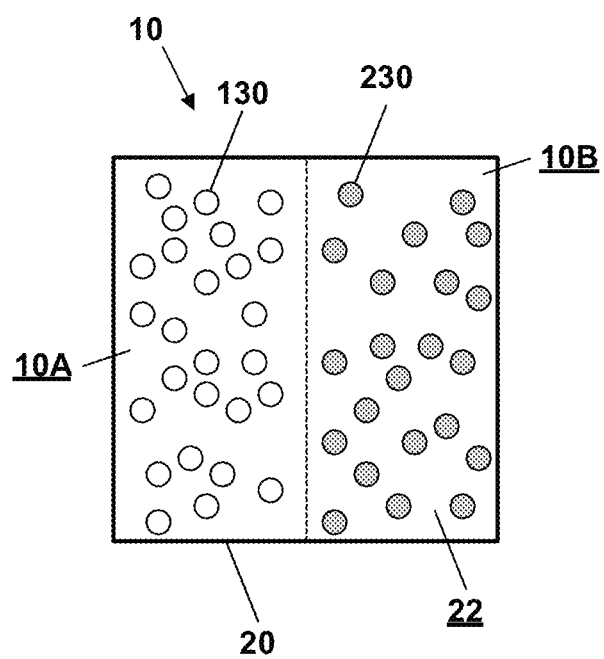
FIG. 5 is a top view of a shock detection substrate according to an additional aspect of the disclosure and incorporating a plurality of different microcapsule types spatially segregated in different regions of a substrate surface.
Figure 6:
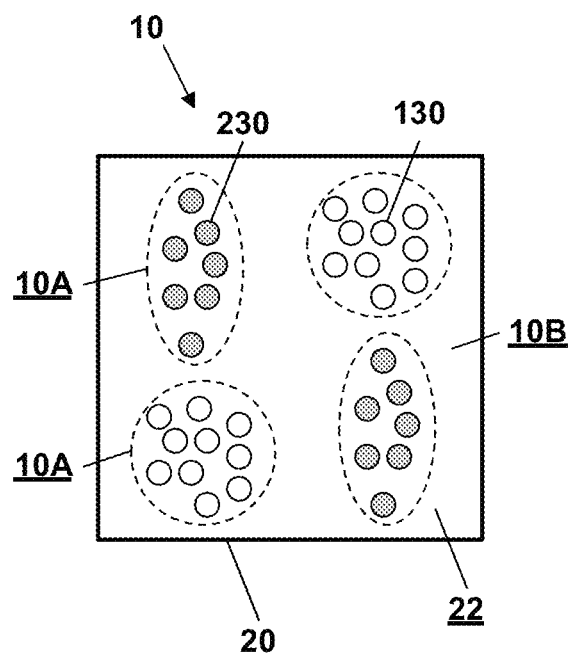
FIG. 6 is a top view of a shock detection substrate according to an additional aspect of the disclosure and incorporating microcapsules in a plurality of different padding protection areas on a substrate surface.

FIGS. 4-6 illustrate some shock-detection substrate 10 embodiments incorporating the different microcapsules 130, 230.

In FIG. 4, the plurality of the first microcapsules 130 and the plurality of the second microcapsules 230 are homogeneously distributed throughout a region of the first substrate 20. The combination of high- and low-impact detection microparticles mixed together provides spatially integrated result over the substrate 20 area. A low impact releases just the first indicator 136, and a high impact releases both the first and second indicators 136, 236. Detection of neither indicator in an area means that the area sustained no impact above the low threshold; detection of just the first indicator 136 in an area means that the area sustained an impact between the low and high thresholds; and detection of at least the second indicator 236 (or both indicators 136, 236) in an area means that the area sustained an impact above the high threshold. As an illustrative example, a yellow optical indicator may be used for the first indicator 136 and a blue optical indicator may be used for the second indicator 236. In such case, a detectable yellow result means an impact was between the low and high impact threshold levels, while a detectable green result (e.g., indicative of blue and yellow mixing) means impact was above the high impact threshold levels. Thus, the shock-detection substrate 10 provides an irreversible spatial contour impact map (which can be integrated over substrate area) showing areas of (i) below low impact, (ii) between high and low impact and (iii) above high impact. In an extension, more contours/impact levels are possible using more distinct indicators having differentiable detectable properties when cumulatively ruptured.

In FIG. 5, the plurality of the first microcapsules 130 and the plurality of the second microcapsules 230 are spatially segregated in separate regions 10A, 10B of the first substrate 20. Such separation into distinct regions 10A, 10B can be used to differentiate different impact levels among them, for example where the different regions 10A, 10B represent more and less impact-sensitive regions of an article incorporating the shock-detection substrate 10 (e.g., a human body part protected by a protective garment incorporating the shock-detection substrate 10). In this embodiment, it is also possible for the first and second detectable properties to be the same (e.g., same colors) or different, because a known, pre-selected spatial segregation of the microcapsules 130, 230 can differentiate the high/low impact results even if the detectable properties are the same.

FIG. 6 illustrates an embodiment in which the microcapsules 130, 230 are spatially positioned on the substrate 20 to define one or more areas 10A containing the microcapsules 130, 230 and one or more areas 10B free (or substantially free) from microcapsules 130, 230. Although FIG. 6 illustrates two types of microcapsules 130, 230, different refinements can include only one or more than two types of microcapsules. In another refinement, the areas 10A can be padding protection areas having a shape corresponding to protective padding for a protective garment (e.g., which facilitates the incorporation of the shock-detection substrate 10 into an existing protective garment, such as when the shock-detection substrate 10 includes a suitable means for attachment 60 for installation). A padding protection area can be a single unitary area in the shape of a protective pad (e.g., the shape of the outer or inner surface thereof, depending on the intended padding surface for attachment), and/or it can be a plurality of areas which collectively are in the shape of a protective pad (e.g., when the padding consists of multiple separate pieces for mounting within a protective garment). In a helmet setting as detailed below, the padding areas can correspond to sections for the back of the head, the sides of the head, the forehead, and/or the dome of the head.

The detectable property associated with the indicator 36 can be a property of the indicator 36 itself and/or a property of the environment surrounding the microcapsule 30 and affected by the indicator 36 after rupture of the microcapsule 30 and release of the indicator 36. The detectable property can variously correspond to an irreversible transition from a first state to a second state for the microcapsule 30 and/or indicator 36 in which the property is (i) detectable in the first state but not the second state, (ii) detectable in the second state but not the first state, or (iii) detectable but different in both states. Detection can be by human inspection (e.g., visual inspection or smelling for optical or olfactory indicators, respectively) or machine-assisted for the particular property being detected. The detectable property can include one or more of an optical property, an olfactory property, a chemical property, an electrical property, and an electromagnetic property associated with the indicator 36.

An optical property can correspond to color change or color generation, electromagnetic radiation emission at one or more wavelengths (e.g., light in the UV, visible, and or IR spectrum), or optical transmission at one or more wavelengths (e.g., in the UV, visible, and or IR spectrum). As noted, optical properties can be detectable by visual inspection (human eye), by conventional optical detection equipment, or both. Example optical indicators include dyes or pigments having a detectable color in the visible spectrum and fluorophores excitable with incident light and producing a detectable UV or visible light emission. Suitable fluorescent probes and indicator dyes (e.g., pH-sensitive, $Ca^{2+}$-sensitive, or otherwise) include fluoresceins, carboxyfluoresceins, hydroxypyrenes, rhodamines, disodium fluorescein, nile red, nile blue, cresyl violet, and acridine orange (e.g., available from Sigma-Aldrich, St. Louis, Mo.). Example calcium indicators (molecular probes) include calcium green, calcium orange, calcium crimson, fluoresceins, furanosines, indocyanines, and rhodamines (e.g., life technologies products available from Thermo Fisher Scientific, Waltham, Mass.). Such dyes, pigments, and/or fluorophores can be dissolved or suspended in a fluid medium contained within the microcapsule 30 prior to rupture and released therefrom after rupture. In some embodiments, the optical indicator can initially be undetectable (e.g., clear or colorless) when inside the microcapsule 30, becoming optically detectable only after rupture and release from the microcapsule 30. For example, the underlying substrate 20 can include an indicator-activating agent (e.g., an acid or base for pH-sensitive indicators or a $Ca^{2+}$-containing substance for $Ca^{2+}$-sensitive indicators), which causes the optical indicator to become optically detectable after release and contact with the activating agent. Alternatively or additionally, other microcapsules containing the indicator-activating agent and having the same or similar rupture characteristics as those containing the optical indicator can be included on the substrate 20 and intermingled with the microcapsules 30 (e.g., where initially segregated indicator and activating agent in different microcapsules combine after rupture to become detectable). In other embodiments, the optical indicator can initially be in a detectable form when inside the microcapsule 30. In such cases, the optical indicator can be masked from detection prior to rupture and release from the microcapsule 30 based on the optical properties of the microcapsule 30 wall. For example, the microcapsule 30 can be formed from a light-absorbing polymer (e.g., poly(pyrrole) which absorbs light across the visible spectrum or other polymer which is suitably doped to absorb light); after microcapsule 30 rupture, the optical indicator is exposed to external (e.g., ambient) light and can be optically detected.

An olfactory property can correspond to the generation of a detectable scent (e.g., by human nose), such as resulting from the release of a scented olfactory indicator from the microcapsule 30 after rupture. Example olfactory indicators include any of a variety of inorganic or organic compounds at a concentration/amount sufficient to generate a detectable scent upon release, for instance linear, cyclic, and/or aromatic organic compounds having one or more aldehyde, ketone, and/or alcohol functional groups such as biacetyl, camphor, or cinnamaldehyde.

A chemical property can correspond to the generation of a detectable chemical property, which itself could be detectable, for example including the release of an acid or base indicator detectable as pH value after rupture. Similarly, the microcapsule 30 rupture event could induce a different detectable chemical property, for example pH change resulting from the release of an acid or base indicator which then induces a color change via a pH indicator external to the ruptured microcapsule 30, for example a pH indicator incorporated on or in the substrate 20 (or 40) surrounding the microcapsule 30.

An electrical property can correspond to the generation of a voltage or current, a change in conductivity, etc. following release of an electrical indicator. Example electrical indicators include (aqueous) solutions with one or more metal-containing compounds such as metal salts (e.g., alkali or alkali earth metal salt with an organic or inorganic anion such as a halogen). For instance, the detection substrate 20 can include wires or other electrical leads that do not form a complete electrically conductive path between electrical input and output regions of the substrate when initially formed. When the electrical indicator is (for example) an aqueous metal salt solution (e.g., sodium chloride) contained in the microcapsule 30, rupture of the microcapsule 30 can release the metal salt, which in turn provides detectable electrical connectivity between the previously unconnected electrical leads.

EXAMPLES

The following examples illustrate the disclosed articles and methods, but are not intended to limit the scope of any claims thereto.

Example 1

Example 1 illustrates the incorporation of a shock-detection substrate 10 spatially positioned into/onto a protective or other garment or wearable article to detect shock experienced by a wearer of the (protective) garment or article and/or to detect shock experienced by the shock-detection substrate itself from a wearer of the article or garment. In various embodiments, the shock-detection substrate can provide an indication when a wearer of the garment or article has sustained a shock or impact at or above a safe level. In other embodiments, the shock-detection substrate can provide an indication when the substrate has reached the end of its useful life (e.g., when the substrate itself provides some padding or cushion functionality such as when it has a foam structure with the microcapsules therein). In some embodiments, the protective garment is a helmet (e.g., sporting helmet such as for football, hockey, biking, skiing, motorcycling, snowmobiling, etc.; combat helmet). In other embodiments, the protective garment is a wearable guard for other than a head body part (e.g., chest, shoulder, back, arm, groin, leg, etc. for sporting in general or a specific sport such as those above). In other embodiments, the garment is a footwear garment (e.g., shoes, boots, etc. for athletic footwear, sporting footwear, casual footwear) and the shock-detection substrate can be a component of the sole (e.g., insole), in particular when it includes a foamed substrate with the microcapsules distributed therein. In other embodiments, the wearable article is a wearable prosthetic (e.g., wearable prosthetic arm, leg, or other limb) and the shock-detection substrate is a component of the prosthetic's comfort padding for interfacing with the wearer's body parts, in particular when it includes a foamed substrate with the microcapsules distributed therein.

Figure 7:
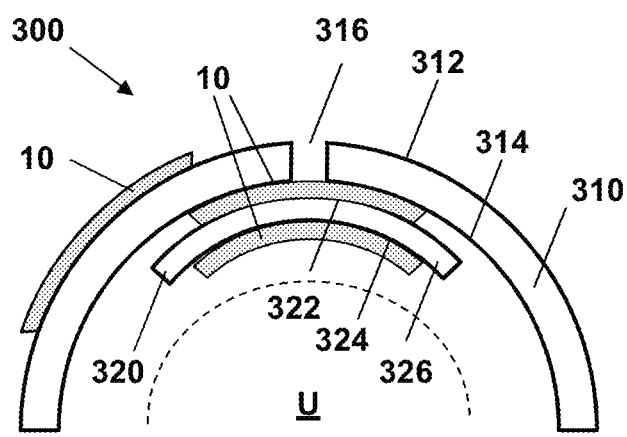
FIG. 7 is a side cross sectional view of a protective garment incorporating a shock detection substrate according to the disclosure.

FIG. 7 illustrates a protective garment 300 according to the disclosure. The protective garment 300 in FIG. 7 is illustrated in a generally curved shape suitable for a helmet, but it can correspond to other garment and wearable article types as noted above. The protective garment 300 includes a protective shell 310 having an outer surface 312 and an opposing inner surface 314. The protective shell 310 is generally a rigid, impact-resistant material such as formed from a plastic/polymeric material or composite (e.g., molded polycarbonate for football helmets). For the protective shell 310, the outer surface 312 is a relative term denoting the external surface exposed to the environment and/or representing the impact surface when the protective garment 300 is worn by a user or wearer U, and the inner surface 314 similarly represents the surface internal to the protective garment 300 and closest to the user U when worn. The protective garment 300 further includes protective padding 320 having an outer surface 322, an opposing inner surface 324, and an interior padding volume 326 between the outer surface 322 and the inner surface 324. The protective padding 320 is mounted at the outer surface 322 thereof to the protective shell 310 at the inner surface 314 thereof (e.g., directly or indirectly with a shock-detection substrate 10 or other intervening component). The protective padding 320 is generally a soft, flexible impact-absorbing material such as formed from polymeric foams, gels, cloth/fabric, inflatable gas (air) bladders, etc. (e.g., example: poly(vinyl nitrile) foam, expanded polypropylene foam of varying densities encased in a shell such as polyethylene for football helmets). Similar to the protective shell 310, the protective padding 320 outer surface 322 is a relative term denoting the surface closest to the protective shell 310 and farthest away from the user U when the protective garment 300, and the inner surface 324 represents the surface internal to the protective garment 300 and closest to the user U when worn. Two surfaces/structures mounted to each other (e.g., the protective shell 310 and the protective padding 320) can be fixedly or removably attached to each other (e.g., generally in a fixed position relative to each other while mounted), either directly or indirectly, such as by any suitable means for attachment. Example means for attachment can include those described above for the shock-detection substrate 10, including adhesive coatings, mechanical fasteners, etc.

As further shown in FIG. 7, the shock-detection substrate 10 can be incorporated into the protective garment 300 at any of a variety of locations. For example, the shock-detection substrate 10 can be positioned at one or more of an interface between the protective shell 310 inner surface 314 and the protective padding 320 outer surface 322, the interior padding volume 326, the protective padding 320 inner surface 324, and the protective shell 310 outer surface 312. The shock-detection substrate 10 can be mounted or adhered to the protective shell 310 and/or protective padding 320 using the means for attachment described above, for example an attachment means 60 incorporated as a component of the substrate 10 and/or as part of the shell 310 or padding 320. In a refinement, the protective shell 310 can include a viewport 316 (e.g., an open area or a transparent window or section of the shell 310) configured to provide optical access from the protective shell 310 outer surface 312 to the interface between the protective shell 310 inner surface 314 and the protective padding 320 outer surface 322. Positioning of a shock-detection substrate 10 at this interface provides a convenient manner for optical detection (visual or otherwise) of an optically detectable property associated with the indicator 36 of the substrate 10 (e.g., line-of-sight inspection of the substrate 10 without having to remove the garment 300 from the user U).

Example 2

Figure 8:
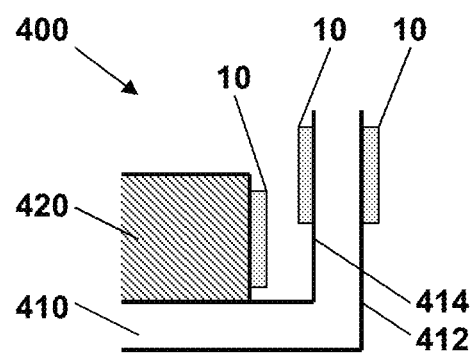
FIG. 8 is a side cross sectional view of a container or electronic apparatus incorporating a shock detection substrate according to the disclosure.

Example 2 illustrates the incorporation of a shock-detection substrate 10 into/onto a shipping or storage container to detect damage resulting from an impact and/or verify the integrity of the container. As illustrated in FIG. 8, a shipping or storage container 400 includes an outer containment structure 410 having an outer surface 412 and an inner surface 414, and the container 400 includes internal contents or components 420 contained therein. The containers 400 can include crates and boxes of cardboard or wood or otherwise. The contents 420 also can include packing inserts (e.g., foamed polymer, cardboard or otherwise) or articles to be stored or shipped. As illustrated, the shock-detection substrate 10 can be mounted/affixed to an interior and/or exterior surface of the container 400 wall 410 and/or the contents 420. Inspection of the shock-detection substrate 10 both before and after a storage time or shipping event can be performed to verify whether the container 400 and/or its contents 420 sustained any substantial shock or impact events during the storage time or shipping event (e.g., if the indicator 36 detectable property is detected afterwards).

Example 3

Example 3 illustrates the incorporation of a shock-detection substrate 10 into/onto an electronic apparatus to detect damage resulting from an impact and/or verify the integrity of the apparatus. As similarly illustrated in FIG. 8, an electronic apparatus 400 includes an outer containment structure 410 having an outer surface 412 and an inner surface 414, and the apparatus 400 includes internal components 420 contained therein. The apparatus 400 can include any electronic apparatus such as a television, a computer monitor, a computer, a tablet computer, a smart phone or other phone, etc. As illustrated, the shock-detection substrate 10 can be mounted/affixed to an interior and/or exterior surface of the apparatus 400 wall 410 and/or the contents 420. Inspection of the shock-detection substrate 10 both before and after a storage time, shipping event, or other usage interval can be performed to verify whether the apparatus 400 sustained any substantial shock or impact events during the time, event, or interval (e.g., if the indicator 36 detectable property is detected afterwards).

Example 4

A shock-detection substrate 10 according to the disclosure can be used to form a dental bite pattern, for example for routine dental diagnostic purposes or for forensic investigation purposes (e.g., to compare with an unknown dental bite pattern on another surface in a method for dental bite pattern validation). For example, biting pressure can be applied from teeth (e.g., of a human or a non-human animal) to the shock-detection substrate 10, which ruptures at least some of the microcapsules 30 and generates the associated detectable property in a spatial pattern corresponding to the dental bite pattern of the teeth.

Example 5

Figure 9:
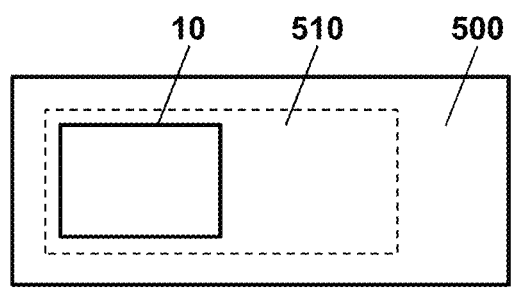
FIG. 9 is a top view of a piece of sporting equipment incorporating a shock detection substrate according to the disclosure.

Example 5 illustrates the incorporation of a shock-detection substrate 10 onto a piece of sporting equipment to detect the force with and/or location at which the sporting equipment strikes a target. As illustrated in FIG. 9, a piece of sporting equipment 500 includes a general area or region 510 where it is intended to strike a target. The equipment 500 can be any sporting equipment intended to strike another object such as a golf club, baseball bat, hockey stick, etc. The shock-detection substrate 10 is affixed on the striking surface 510 to determine where and/or how hard the equipment 500 contacts its intended target (e.g., golf ball, baseball, hockey puck, etc.).

Example 6

A shock-detection substrate 10 according to the disclosure can be used to provide a tamper-proof recording of a handwritten signature. The shock-detection substrate 10 can serve as a pressure-sensitive signature strip such that when a ball point pen or other sharp object is used for signing a signature, the underlying microcapsules 30 burst and result in a permanent signature that cannot be erased. Any further pressure would destroy the originally imprinted signature. The signature strip can be incorporated into any physical document intended to receive a signature (e.g., a legal instrument such as a contract or check, or other written document), for example where paper or other writing substrate is the first substrate 20, and microcapsules 30 are incorporated on or in at least a portion thereof to form the shock-detection substrate 10. The tamper-proof signature can be used in a method of signature validation by comparing the signature on the shock-detection substrate 10 with a known reference signature of the signer.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the articles, compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

PARTS SUMMARY

10: shock-detection substrate
10A, 10B: different regions of shock-detection substrate
20: first substrate
22, 24, 26: top surface, bottom surface, and interior volume of first substrate
30, 130, 230: microcapsules
32, 34, 36 (132, 134, 136; 232, 234, 236): outer shell, interior volume, and contained indicator of microcapsules
40: second substrate
42, 44, 46: top surface, bottom surface, and interior volume of second substrate
50: microcapsule layer between substrates
60: means for attachment
300: protective garment for user U
310: protective shell
312, 314: outer surface, inner surface of protective shell
316: viewport
320: protective padding
322, 324, 326: outer surface, inner surface, and interior volume of protective padding 400: container or electronic apparatus
410: outer containment structure
412, 414: outer surface, inner surface of outer containment structure
420: internal contents or components
500: sports striking equipment
510: striking surface

REFERENCES

1. Kijewska et al., Chem. Eur. J., 18:310-320 (2012)
2. Tiarks et al., Langmuir, 17:908-918 (2001)
3. Kamata et al., J. Am. Chem. Soc., 125:2384-2385 (2003)
4. Wang et al., Chem. Mater., 20:848-858 (2008)

What is claimed is:

1. An irreversible dosimetric shock-detection substrate comprising:
   (a) a first substrate comprising a flexible foam, the first substrate having (i) a top surface, (ii) an opposing bottom surface, and (iii) an interior substrate volume between the top surface and the bottom surface;
   (b) a plurality of microcapsules each comprising (i) an outer shell defining an interior volume and (ii) an indicator contained in the interior volume, wherein:
      the microcapsules are positioned at the interior substrate volume of the first substrate flexible foam, and
      each microcapsule has a characteristic impact threshold prior to rupture of the microcapsule and release of the indicator from the interior volume to generate an irreversible change in a detectable property associated with the indicator; and
   (c) a means for attachment on one or both of the first substrate top surface and the first substrate bottom surface.

2. The shock-detection substrate of claim 1, wherein the characteristic impact threshold of the microcapsule has been selected by controlling one or more of reaction solvent, polymerization initiator, monomer, ionic strength, reaction medium pH, reaction temperature, reaction time, and UV light exposure during a polymerization process forming the microcapsule.

3. The shock-detection substrate of claim 1, wherein the detectable property is selected from the group consisting of an optical property, an olfactory property, a chemical property, an electrical property, an electromagnetic property, and combinations thereof.

4. The shock-detection substrate of claim 1, wherein the plurality of microcapsules comprises:
   (A) a plurality of first microcapsules containing a first indicator therein and having a first characteristic impact threshold; and
   (B) a plurality of second microcapsules containing a second indicator therein and having a second characteristic impact threshold;
   wherein:
      the detectable property of the first indicator is different from the detectable property of the second indicator, and
      the first characteristic impact threshold is different from the second characteristic impact threshold.

5. The shock-detection substrate of claim 4, wherein the plurality of the first microcapsules and the plurality of the second microcapsules are homogeneously distributed throughout a region of the first substrate.

6. The shock-detection substrate of claim 4, wherein the plurality of the first microcapsules and the plurality of the second microcapsules are spatially segregated in separate regions of the first substrate.

7. The shock-detection substrate of claim 1, wherein the plurality of microcapsules is spatially positioned on the substrate to define one or more padding protection areas containing the plurality of microcapsules, the one or more padding protection areas having a shape corresponding to protective padding for a protective garment.

8. The shock-detection substrate of claim 1, wherein the flexible foam comprises an open cell foam network.

9. The shock-detection substrate of claim 1, wherein the flexible foam comprises a material selected from the group consisting of a polyurethane, a poly(vinyl nitrile), a polyethylene, a polypropylene, a polystyrene, a poly(ethylene-vinyl acetate), a poly(vinyl chloride), a poly(acrylonitrile-butadiene-styrene), a polyimide, a polyetherimide, a polyphenyleneoxide, a polychloroprene, a polysiloxane, a polyepoxide, a polyester, a phenolic resin, a urea-formaldehyde resin, a cellulose acetate, and combinations thereof.

10. The shock-detection substrate of claim 1, wherein the flexible foam comprises at least one of a polyurethane, a poly(vinyl nitrile), and a poly(ethylene-vinyl acetate).

11. The shock-detection substrate of claim 1, wherein:
   (i) the outer shell of the microcapsules comprises silica; and
   (ii) the indicator comprises an optical indicator contained in a fluid medium and having an optical detectable property.

12. A footwear garment comprising the shock-detection substrate of claim 1 spatially positioned in or on the footwear garment to detect shock experienced by the shock-detection substrate from a wearer of the footwear garment.

13. A wearable prosthetic comprising the shock-detection substrate of claim 1 spatially positioned in or on the prosthetic to detect shock experienced by the shock-detection substrate from a wearer of the prosthetic.

14. A protective garment comprising the shock-detection substrate of claim 1 spatially positioned in or on the protective garment to detect shock experienced by a wearer of the protective garment.

15. A shipping or storage container comprising the shock-detection substrate of claim 1 spatially positioned in or on the container to detect shock experienced by the container during shipment or storage.

16. An electronic apparatus comprising the shock-detection substrate of claim 1 spatially positioned in or on the apparatus to detect shock experienced by the apparatus during shipment, storage, or use.

17. A method for forming a dental bite pattern, the method comprising:
   (a) providing the shock-detection substrate of claim 1; and
   (b) applying biting pressure from teeth to the shock-detection substrate, thereby rupturing at least some of the microcapsules and generating the associated detectable property in a spatial pattern corresponding to the dental bite pattern of the teeth.

18. A piece of sports striking equipment comprising the shock-detection substrate of claim 1 spatially positioned in or on the equipment to detect shock experienced by the equipment during use.

19. A method for validating a handwritten signature, the method comprising:
   (a) providing a physical written document comprising the shock-detection substrate of claim 1;

(b) receiving a handwritten signature on the shock-detection substrate to form tamper-proof recording of the handwritten signature; and (c) comparing the tamper-proof recording of the handwritten signature with a known reference of the handwritten signature.

20. A protective garment comprising:

(a) a protective shell having (i) an outer surface and (ii) an opposing inner surface;

(b) protective padding having (i) an outer surface, (ii) an opposing inner surface, and (iii) an interior padding volume between the outer surface and the inner surface, wherein the protective padding is mounted at the outer surface thereof to the protective shell at the inner surface thereof; and (c) the shock-detection substrate of claim 1 positioned at one or more of: (i) an interface between the protective shell inner surface and the protective padding outer surface, (ii) the interior padding volume, (iii) the protective padding inner surface, and (iv) the protective shell outer surface.

21. The protective garment of claim 20, wherein the protective garment is a helmet.

22. The protective garment of claim 20, wherein the protective garment is a wearable guard for other than a head body part.

23. The protective garment of claim 20, wherein the protective shell comprises a viewport configured to provide optical access from the protective shell outer surface to the interface between the protective shell inner surface and the protective padding outer surface.

24. The protective garment of claim 20, wherein the shock-detection substrate is positioned at the interface between the protective shell inner surface and the protective padding outer surface.

25. The protective garment of claim 20, wherein the shock-detection substrate is positioned at the protective padding inner surface.

26. A method for detecting impact on a protective garment worn by a user, the method comprising:

(a) wearing the protective garment according to claim 20;

(b) impacting the protective garment;

(c) interrogating the means for detecting impact of the protective garment after (b) to determine whether the protective garment has sustained an impact force exceeding a characteristic impact threshold of the microcapsules.

27. The method of claim 25 further comprising:

(d) if the protective garment has sustained an impact force exceeding the characteristic impact threshold, performing one or more of (i) removing the user from an ongoing impact environment, (ii) investigating the user for an impact-related injury, and (iii) treating the user for an impact-related injury.

28. A method for equipping a protective garment with a means for detecting impact, the method comprising:

(a) providing a protective garment comprising:

(i) a protective shell having (A) an outer surface and (B) an opposing inner surface, and (ii) protective padding having (A) an outer surface, (B) an opposing inner surface, and (C) an interior padding volume between the outer surface and the inner surface;

(b) attaching the shock-detection substrate of claim 1 to one or more of:

(i) the protective padding outer surface, and (ii) the protective padding inner surface; and (c) mounting the protective padding at the outer surface thereof to the protective shell at the inner surface thereof.

29. A kit comprising:

(a) a shock-detection substrate of claim 1; and (b) protective padding sized and shaped for insertion into a protective shell of a protective garment, the protective padding having (i) an outer surface, (ii) an opposing inner surface, and (iii) an interior padding volume between the outer surface and the inner surface.

30. An irreversible dosimetric shock-detection substrate comprising:

(a) a first substrate comprising a flexible foam, the first substrate having (i) a top surface, (ii) an opposing bottom surface, and (iii) an interior substrate volume between the top surface and the bottom surface; and (b) a plurality of microcapsules each comprising (i) an outer shell comprising silica and defining an interior volume and (ii) an indicator contained in the interior volume, wherein:

the microcapsules are positioned at the interior substrate volume of the first substrate flexible foam, and each microcapsule has a characteristic impact threshold prior to rupture of the microcapsule and release of the indicator from the interior volume to generate an irreversible change in a detectable property associated with the indicator.

31. The shock-detection substrate of claim 30, wherein the indicator comprises an optical indicator contained in a fluid medium and having an optical detectable property.

* * * * *